United States Patent
Dunne et al.

(10) Patent No.: US 8,226,746 B2
(45) Date of Patent: *Jul. 24, 2012

(54) INDIRECTLY HEATED TEMPERATURE CONTROLLED ADSORBER FOR SORBATE RECOVERY

(75) Inventors: Stephen R. Dunne, Algonquin, IL (US); David A. Wegerer, Lisle, IL (US)

(73) Assignee: UOP LLC, Des Plaines, IL (US)

( * ) Notice: Subject to any disclaimer, the term of this patent is extended or adjusted under 35 U.S.C. 154(b) by 399 days.

This patent is subject to a terminal disclaimer.

(21) Appl. No.: 12/555,445

(22) Filed: Sep. 8, 2009

(65) Prior Publication Data

US 2010/0150812 A1    Jun. 17, 2010

Related U.S. Application Data

(60) Provisional application No. 61/138,325, filed on Dec. 17, 2008.

(51) Int. Cl.
*B01D 53/04* (2006.01)

(52) U.S. Cl. ............... 95/114; 95/122; 95/126; 95/142; 95/148

(58) Field of Classification Search .............. 95/114, 95/115, 122, 126, 129, 134, 139, 141, 142, 95/148; 96/126, 146
See application file for complete search history.

(56) References Cited

U.S. PATENT DOCUMENTS

| | | | |
|---|---|---|---|
| 2,137,605 A | | 11/1938 | Derr |
| 3,594,983 A | * | 7/1971 | Yearout ........................ 95/97 |
| 3,664,095 A | | 5/1972 | Asker et al. |
| 3,683,591 A | * | 8/1972 | Glav ............................ 95/93 |
| 3,734,293 A | * | 5/1973 | Biskis ....................... 210/185 |
| 4,297,172 A | | 10/1981 | Kyle |
| 4,351,732 A | | 9/1982 | Psaras et al. |
| 4,418,545 A | | 12/1983 | Markfort |
| 4,451,270 A | | 5/1984 | Roman |
| 4,479,814 A | | 10/1984 | Oliker |
| 4,594,856 A | | 6/1986 | Rothmeyer |
| 4,726,818 A | | 2/1988 | Yeung et al. |
| 4,846,135 A | | 7/1989 | Tiphaine |

(Continued)

FOREIGN PATENT DOCUMENTS

DE      3501216 A1    7/1986

(Continued)

OTHER PUBLICATIONS

U.S. Appl. No. 12/637,829, filed Dec. 15, 2009, Wegerer.

(Continued)

*Primary Examiner* — Frank Lawrence, Jr.
(74) *Attorney, Agent, or Firm* — Mark Goldberg

(57) ABSTRACT

Systems and processes are provided that relate to the recovery of sorbates in processes utilizing temperature controlled adsorption. Sorbate recovery can include providing a temperature controlled adsorber that is undergoing a regeneration cycle after undergoing an adsorption cycle. The temperature controlled adsorber can have one or more adsorption flow passages and one or more heat transfer flow passages. The one or more adsorption flow passages can contain an adsorptive material coating with a sorbate adsorbed thereto. A heating fluid can be provided to the one or more heat transfer flow passages of the temperature controlled adsorber. A regeneration stream can be provided to the one or more adsorption flow passages of the temperature controlled adsorber. The adsorptive material coating can be regenerated by removing the sorbate from the temperature controlled adsorber to produce a regeneration effluent stream.

21 Claims, 4 Drawing Sheets

U.S. PATENT DOCUMENTS

| | | |
|---|---|---|
| RE33,352 E | 9/1990 | Roman et al. |
| 5,116,510 A | 5/1992 | Sircar et al. |
| 5,571,477 A | 11/1996 | Nagy et al. |
| 5,669,962 A | 9/1997 | Dunne |
| 5,733,451 A * | 3/1998 | Coellner et al. ............ 210/496 |
| 5,768,904 A | 6/1998 | Tagamolila et al. |
| 5,802,870 A | 9/1998 | Arnold et al. |
| 5,823,003 A | 10/1998 | Rosser, Jr. et al. |
| 5,845,507 A | 12/1998 | Critoph et al. |
| 5,953,927 A | 9/1999 | Tagamolila et al. |
| 6,372,026 B1 | 4/2002 | Takemasa et al. |
| 6,423,275 B1 | 7/2002 | D'Souza |
| 6,591,630 B2 | 7/2003 | Smith et al. |
| 6,601,404 B1 | 8/2003 | Roderick |
| 6,607,583 B2 | 8/2003 | Cowles et al. |
| 6,849,568 B2 | 2/2005 | Yan |
| 7,410,533 B2 | 8/2008 | Yabu |
| 7,422,993 B2 | 9/2008 | Tadewaki et al. |
| 7,497,089 B2 | 3/2009 | Kakiuchi et al. |
| 7,578,143 B2 | 8/2009 | Critoph et al. |
| 7,704,305 B2 | 4/2010 | Nishida |
| 7,795,479 B1 | 9/2010 | Wegerer et al. |
| 2003/0037672 A1* | 2/2003 | Sircar ............................ 95/96 |
| 2004/0089001 A1 | 5/2004 | Kakiuchi et al. |
| 2005/0006310 A1 | 1/2005 | Agrawal et al. |
| 2005/0252235 A1 | 11/2005 | Critoph et al. |
| 2006/0086125 A1 | 4/2006 | Sueoka et al. |
| 2006/0249020 A1 | 11/2006 | Tonkovich et al. |
| 2007/0000769 A1 | 1/2007 | Brown |
| 2007/0238906 A1 | 10/2007 | Brown et al. |
| 2008/0023181 A1 | 1/2008 | Dunne et al. |
| 2008/0034785 A1 | 2/2008 | Yanagi |
| 2008/0039665 A1 | 2/2008 | Brown et al. |
| 2008/0176303 A1 | 7/2008 | Massie |
| 2008/0245653 A1 | 10/2008 | Zhong et al. |
| 2009/0025403 A1 | 1/2009 | Kakiuchi et al. |
| 2010/0132254 A1 | 6/2010 | Wegerer et al. |
| 2010/0132548 A1 | 6/2010 | Dunne et al. |
| 2010/0137657 A1 | 6/2010 | Wegerer et al. |
| 2010/0224565 A1* | 9/2010 | Dunne et al. ................ 210/670 |

FOREIGN PATENT DOCUMENTS

| | | |
|---|---|---|
| DE | 3702190 A1 | 8/1988 |
| EP | 0373538 A1 | 6/1990 |
| EP | 0394947 A2 | 10/1990 |
| EP | 1873462 A1 | 1/2008 |
| FR | 2619106 A1 | 2/1989 |
| FR | 2669087 A1 | 5/1992 |
| FR | 2699087 A1 | 6/1994 |
| JP | 60129116 | 7/1985 |
| JP | 2000018767 A | 1/2000 |
| WO | WO 95/30469 A1 | 11/1995 |
| WO | WO 03/008091 A1 | 1/2003 |
| WO | WO 2008/155543 A2 | 12/2008 |
| WO | WO 2009/002893 A2 | 12/2008 |

OTHER PUBLICATIONS

U.S. Appl. No. 12/337,248, filed Dec. 17, 2008, Dunne.
U.S. Appl. No. 12/337,154, filed Dec. 17, 2008, Wegerer.
U.S. Appl. No. 12/555,450, filed Sep. 8, 2009, Wegerer.
"Adsorption of gas mixtures in TSA adsorbers under various heat removal conditions", Clausse, Chemical Engineering Science 59 (2004) 3657-3670.
"Internal heat and mass transfer during thermal desorption", Kuatbekov, chemical abstract, Tear Osn Khim Tekhnol 1973, vol. 7, No. 3, pp. 429-433.
"Isoconversional kinetic analysis of isothermal selective ethanol adsorption on zeolite type NaZSM-5", Adnadevic, Chem. Eng. Technol., 2007, 30, No. 9, 1228-1234.
"Isothermal composite adsorbent. Part I: Thermal characterisation", Meljac, Applied Thermal Engineering 27 (2007) 1009-1016.
"Production of cold heat energy by alcohol/activated carbon adsorption . . . ", Kanamori, Journal of Chemical Engineering of Japan, vol. 30, No. 3, 1997.
"TSA process with indirect heating and cooling: parametric analysis and scaling-up to practical sizes", Bonjour, Chemical Engineering and Processing 44 (2005) 969-977.
Karim, "Comparison of wall-coated and packed-bed reactors for steam reforming of methanol", Catalysis Today 110 (2005) 86-91.

* cited by examiner

US 8,226,746 B2

INDIRECTLY HEATED TEMPERATURE CONTROLLED ADSORBER FOR SORBATE RECOVERY

CROSS-REFERENCE TO RELATED APPLICATION

This application claims priority from Provisional Application No. 61/138,325 filed Dec. 17, 2008, the contents of which are hereby incorporated by reference.

BACKGROUND OF THE INVENTION

Systems and processes disclosed herein relate to the recovery of sorbates that are removed from process streams by adsorption.

The separation of specific components of process streams in certain applications can be accomplished by the use of adsorption to remove the desired component, followed by recovery of the component during regeneration of the adsorbent. Process streams are typically liquid or gaseous, and can have a wide variety of compositional components depending upon the industrial application of the process.

Packed beds of adsorbent materials are typically used in adsorption processes. Adsorbent materials are generally in the form of spherical beads, or pellets. Adsorbent materials are typically oxygen-containing compounds, carbon-containing compounds, or polymer-based compounds. Oxygen-containing compounds can be, for example, hydrophilic and polar, including materials such as silica gel and zeolites. Carbon-based compounds can be, for example, hydrophobic and non-polar, including materials such as activated carbon and graphite. Polymer-based compounds can be, for example, polar or non-polar functional groups in a porous polymer matrix.

Typical adsorption processes utilizing packed beds can be thermal (temperature) swing adsorption (TSA) processes or pressure swing adsorption (PSA) processes. In operation, a process stream is introduced into a packed bed, and the adsorbent material contained therein removes a desired component, known as the sorbate, from the stream as it filters through the packed bed. After a given time period, the adsorbent material becomes saturated with the sorbate, and the adsorption process must be halted in order to regenerate the adsorbent and remove the sorbate. PSA processes utilize a de-pressurized regeneration gas that is introduced to the packed bed in a direction reverse to the flow of the process stream. After a regeneration cycle is complete, a new adsorption cycle can begin. TSA processes utilize heat to remove the sorbate from the adsorbent material. The heat in a typical TSA process is added through the regeneration stream. Thus, the regeneration or purge gas can be utilized to supply all of the heat required to heat the vessel, bed supports, and the adsorbent, as well a providing the energy to desorb the sorbate from the adsorbent. A large volume of regeneration gas is necessary to accomplish this task, which results in a very dilute regeneration effluent stream, which increases the cost of processes utilized to recover the sorbate from the regeneration effluent stream.

BRIEF SUMMARY

The systems and processes disclosed herein relate to the adsorption treatment of process streams to remove a compositional component therefrom in the form of a sorbate, and to the recovery of the sorbate during regeneration of the adsorbent material.

In one aspect, a process for sorbate recovery in the adsorption treatment of a process stream is provided that includes providing a temperature controlled adsorber that is undergoing a regeneration cycle after undergoing an adsorption cycle. The temperature controlled adsorber can have one or more adsorption flow passages and one or more heat transfer flow passages. The one or more adsorption flow passages can contain an adsorptive material coating with a sorbate adsorbed thereto. A heating fluid can be provided to the one or more heat transfer flow passages of the temperature controlled adsorber. A regeneration stream can be provided to the one or more adsorption flow passages of the temperature controlled adsorber. The adsorptive material coating can be regenerated by removing the sorbate from the temperature controlled adsorber to produce a regeneration effluent stream. The quantity of purge or regeneration gas in the regeneration stream may be minimized under certain conditions and under certain conditions there may be no need for a regeneration stream at all.

In another aspect, a process for sorbate recovery in the adsorption treatment of a process stream is provided that includes providing a temperature controlled adsorber that is undergoing a regeneration cycle after undergoing an adsorption cycle. The temperature controlled adsorber can have one or more adsorption flow passages and one or more heat transfer flow passages. The one or more adsorption flow passages can contain an adsorptive material coating with a sorbate adsorbed thereto. A heating fluid can be provided to the one or more heat transfer flow passages of the temperature controlled adsorber. The heating fluid can provide heat to the one or more adsorption flow passages of the temperature controlled adsorber by indirect heat exchange. A regeneration stream can be provided to the one or more adsorption flow passages of the temperature controlled adsorber. Under certain conditions a regeneration stream is not needed at all. The regeneration of the process stream passages can be accomplished without a purge. The adsorptive material coating can be regenerated by removing the sorbate from the temperature controlled adsorber to produce a regeneration effluent stream.

BRIEF DESCRIPTION OF THE DRAWINGS

Specific examples have been chosen for purposes of illustration and description, and are shown in the accompanying drawings, forming a part of the specification.

FIG. 2b is a close-up view of a portion of FIG. 2a.

FIG. 2c is a close-up view of another portion of FIG. 2a.

FIG. 3 is a perspective view of a portion of a temperature controlled adsorber of FIG. 2a.

DETAILED DESCRIPTION

The systems and processes disclosed herein relate to the adsorption treatment of process streams to remove a compositional component therefrom, and more particularly to the recovery of sorbates in processes utilizing temperature controlled adsorption. The compositional component of the process stream that is adsorbed to produce a sorbate can include an impurity, a contaminant, a valuable compound, a regulated compound, or any other component that can be removed from a process stream through an adsorption process. Examples of potential sorbates that can be recovered include, but are not limited to, mercury, one or more volatile organic compounds (VOCs), water, $CO_2$, $NO_x$, one or more halocarbon refrigerants, and propylene.

Figure 1:
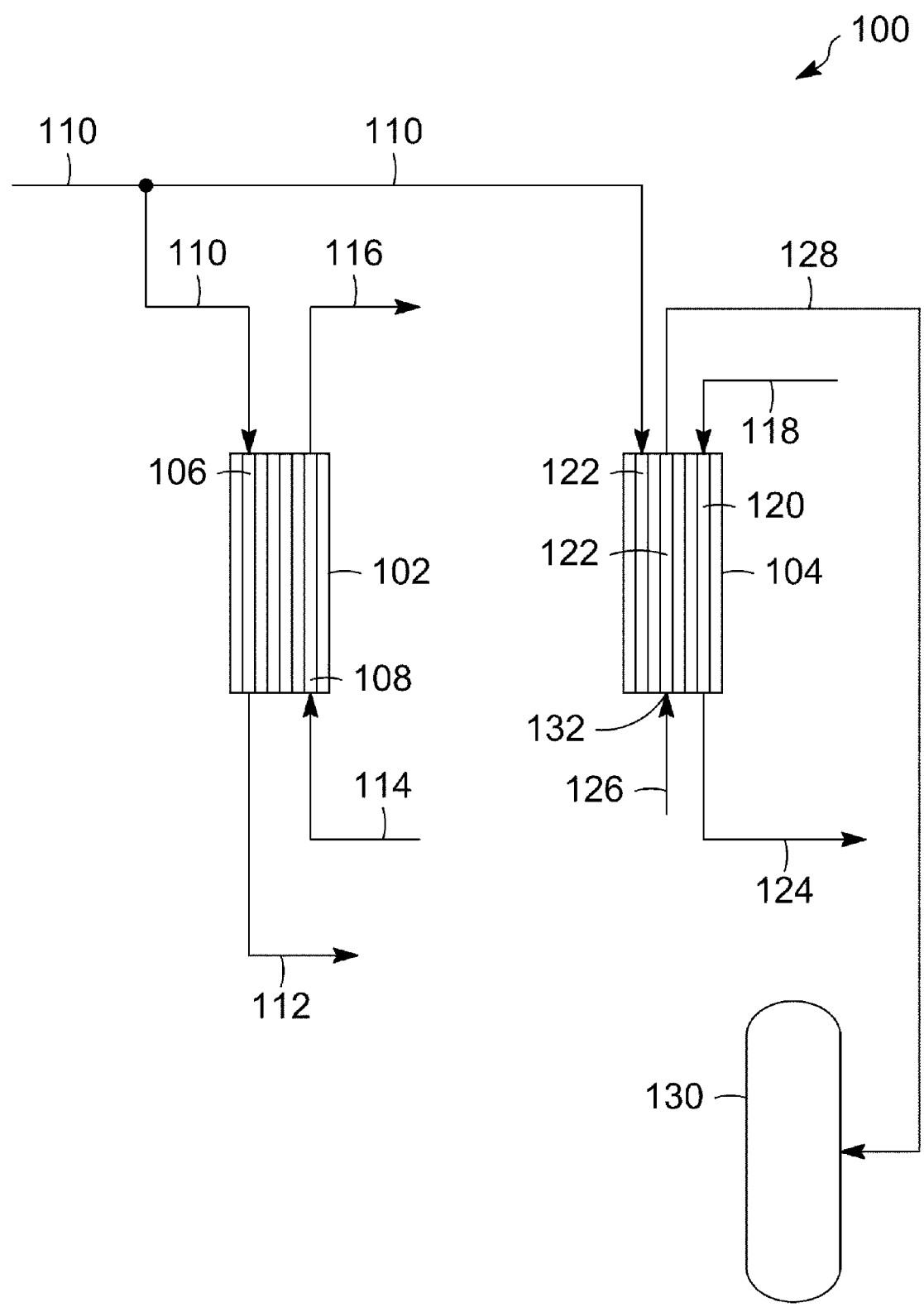
FIG. 1 illustrates a simplified process flow diagram for a sorbate recovery process including temperature controlled adsorbers.

FIG. 1 illustrates a process for adsorption treatment of a process stream 110, the process being indicated generally at 100. As shown in FIG. 1, the adsorption treatment process 100 includes a first temperature controlled adsorber 102, and a second temperature controlled adsorber 104. Temperature controlled adsorbers 102 and 104 are preferably adsorbent containing contactors having internal indirect heat transfer passages. With an indirectly heated or cooled adsorber, heat transfer streams can be introduced that remove or supply heat but do not become part of the process stream or the regeneration effluent stream. Owing to the ability to supply heat through streams other than a process stream or a regeneration stream, the regeneration effluent stream flows can be minimized and can have a much higher concentration of sorbates than can be achieved in conventional TSA processes.

FIGS. 2a through 2d, 3 and 4 illustrate one example of a temperature controlled adsorber 40, which can be utilized in the process of FIG. 1 as either first temperature controlled adsorber 102, second temperature controlled adsorber 104, or preferably both. Temperature controlled adsorber 40 is a plate-fin type heat exchanger with one or more adsorption flow passages 53 and one or more heat transfer flow passages 55. The adsorption flow passages 53 contain an adsorptive material coating 46 that is applied by a wash-coating process. During the wash-coating process, the adsorption flow passages 53 are wash coated with a wash-coating fluid that contains an adsorbent material suitable for adsorption of the desired sorbate, which can include, for example oxygen-containing compounds, carbon-containing compounds, or polymer-based compounds. The wash-coating fluid can also contain an organic polymer system and an organic solvent or carrier fluid. In one example, adsorptive material coating 46 can contain a polymer and a molecular sieve, such as, for example, a zeolite.

A wash-coating process can comprise a step of heating a component to be coated, a step of contacting the surface of the component with a slurry comprising an adsorbent and a binder to form the adsorptive material coating 46, and a step of hardening the adsorptive material coating 46. For some applications, the step of contacting may comprise dipping the surface into the slurry or spraying the surface with the slurry.

The adsorptive material coating 46 may have an adsorptive coating thickness 77 (see FIG. 3) of between about 0.004 inches (0.010 cm) and about 0.052 inches (0.13 cm), preferably from about 0.014 inches (0.035 cm) to about 0.023 inches (0.058 cm). The adsorptive coating thickness 77 may be measured through the adsorptive material coating 46 and about perpendicular to the adsorption zone fin 58. The adsorptive coating thickness 77 may vary with application and may depend on factors including the dimensions of the adsorption zone fins 58, the desired dimensions of the adsorption flow passage 55 and the application. US 2008/0023181 A1, the disclosure of which is hereby incorporated by reference in its entirety, describes the rudiments of the wash-coating process and some of the benefits that ensue in sorption cooling systems.

As illustrated in FIGS. 2a-2d, adsorption heat exchanger 40 can comprise at least one adsorption layer 50, at least one heat transfer layer 51 and a separator plate 52 positioned between and in contact with the adsorption layer 50 and the heat transfer layer 51. The adsorption heat exchanger 40 can comprise a plurality of adsorption layers 50 and a plurality of heat transfer layers 51. The adsorption layers 50 and heat transfer layers 51 may be positioned in a stacked arrangement of alternating adsorption layers 50 and heat transfer layers 51. In other words, one adsorption layer 50 may be positioned between two heat transfer layers 51; and one heat transfer layer 51 may be positioned between two adsorption layers 50. The adsorption heat exchanger 40 can comprise a plurality of separator plates 52 positioned such that one separator plate 52 is between and in contact with each adsorption layer/heat transfer layer pair. In other words, the separator plate 52 may be positioned between the adsorption layer 50 and the heat transfer layer 51. A pair of separator plates 52 are shown spaced by a distance 75 in FIG. 2d. As defined herein, an adsorption layer/heat transfer layer pair may comprise an adsorption layer 50 and a heat transfer layer 51 positioned adjacent to one another.

The adsorption layer 50 may provide an adsorption flow passage 53 through the adsorption heat exchanger 40. The adsorption flow passage 53 may be in a direction parallel to an adsorption flow line 54. The heat transfer layer 51 may define a heat transfer flow passage 55 through the adsorption heat exchanger 40. The heat transfer flow passage 55 may be in a direction parallel to a heat transfer flow line 56. The adsorption flow line 54 may be about 90° from the heat transfer flow line 56. This type of system provides cross flow heat exchange. In alternative examples, an adsorption heat exchanger can operate with either parallel or counter flow heat transfer.

Figure 3:
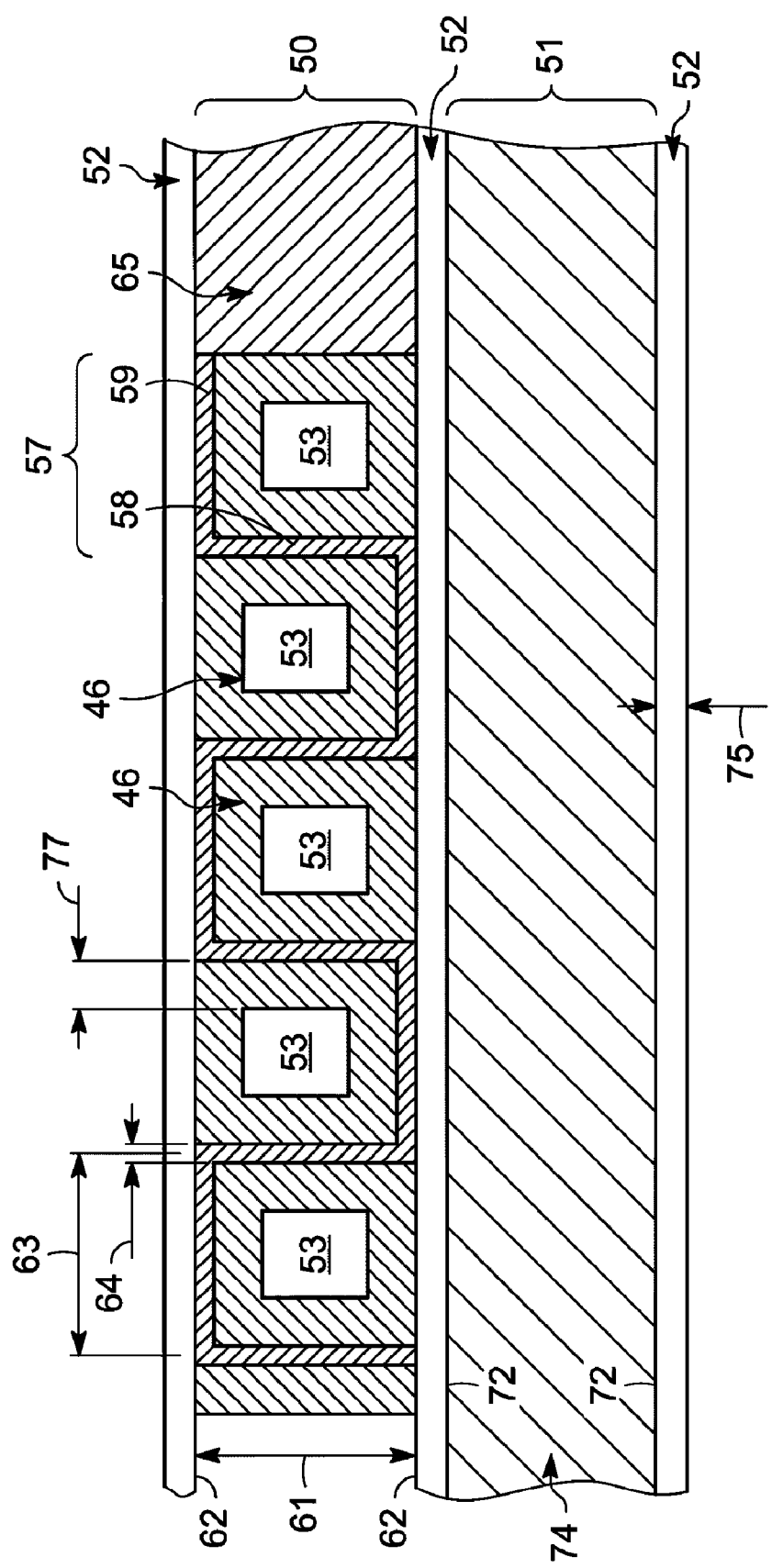

As depicted in FIG. 3, the adsorption layer 50 can include an adsorption zone corrugated sheet 57 and the adsorptive material coating 46. The adsorption zone corrugated sheet 57 may be in contact with and extend between two separator plates 52. The adsorption zone corrugated sheet 57 may comprise a plurality of adsorption zone fins 58 and a plurality of adsorption zone contact portions 59. The adsorption zone fin 58 may be the portion of the adsorption zone corrugated sheet 57 that is perpendicular to and extends between the separator plates 52. The adsorption zone contact portion 59 may be the portion of the adsorption zone corrugated sheet 57 that is parallel to and in contact with the separator plate 52.

Figure 2A:
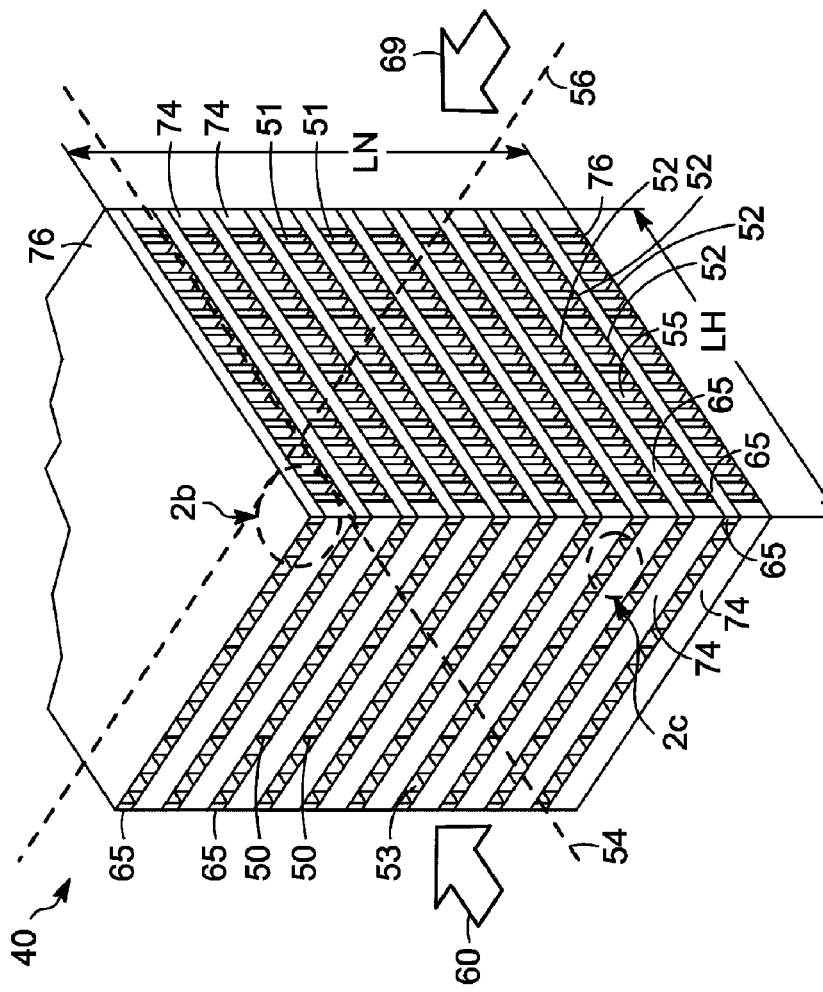
FIG. 2a is a perspective view of a temperature controlled adsorber that can be used in the process of FIG. 1.

The adsorption zone fins 58 may be positioned about perpendicular to the separator plates 52 and may extend about parallel to the adsorption flow line 54. The adsorption zone fins 58 may direct the flow of an adsorbate rich stream 60, as shown in FIG. 2a, through the adsorption heat exchanger 40 and may provide a support for at least a portion of the adsorptive material coating 46. The adsorption zone fin 58 may be in contact with and extend between two separator plates 52. The adsorption fin height 61 may vary with application and may depend on factors including the composition of the adsorption zone fin 58 and the application. The adsorption fin thickness 64 may vary with application and may depend on factors including the composition of the adsorptive material coating 46 and the application. The density of adsorption zone fins (fins/inch) may vary with application and may depend on factors including the thickness of the adsorptive material coating 46 and the desired volume of the adsorption flow passage 53. The density of the adsorption zone fins 58 may be defined as the number of fins per inch of adsorption layer width as measured perpendicular to the adsorption flow line 54 and parallel to the separator plate 52.

The adsorption zone contact portions 59 may be positioned about parallel to and in contact with the separator plates 52. The adsorption zone contact portions 59 may be brazed to an adsorption zone facing side 62 of the separator plates 52. The adsorption zone contact portions 59 may provide a support for at least a portion of the adsorptive material coating 46, as depicted in FIG. 3. In other words, one side of the adsorption zone contact portion 59 may be brazed to the separator plate 52 and the other side may be coated with the adsorptive material coating 46. The adsorption contact width 63 is not an independent parameter. Once the density of the adsorption zone fins 58 and the adsorption fin thickness 64 have been specified the adsorption contact width 63 is a determinate value. The adsorption contact portion width 63 may vary and may depend on the desired density of the adsorption zone fins 58. The adsorption contact portion width 63 may be inversely proportion to the density of the adsorption zone fins 58.

For some applications, in lieu of the adsorption zone corrugated sheet 57, the adsorption layer 50 may comprise a plurality of adsorption zone fins 58 brazed directly to the separator plates 52. The adsorption zone fins 58 of the adsorption layer 50 may increase the surface area available for adsorptive material coating 46, thereby enhancing the adsorption/desorption efficiency of the adsorption heat exchanger 40.

The adsorption layer 50 may include two adsorption zone header bars 65, as depicted in FIG. 2a. The adsorption zone header bars 65 may be positioned parallel to the adsorption flow line 54. One adsorption zone header bar 65 may be positioned at one side of the adsorption layer 50 and the other adsorption zone header bar 65 may be positioned at the opposing side of the adsorption layer 50. The adsorption zone header bars 65 may be brazed to the separator plates 52 and may provide structural support to the adsorption heat exchanger 40.

The adsorption zone corrugated sheet 57, the adsorption zone fin 58, the adsorption zone contact portion 59 and adsorption zone header bar 65 each may comprise a material, such as but not limited to, aluminized Mylar®, a polymer composite, or a metal. Mylar® is a polyester film produced by E.I. Du Pont De Nemours and Company. Useful metals may include aluminum, copper, titanium, brass, stainless steel, other light metals and alloys with high conductivity, and graphite fiber composite materials. Components of the adsorption layer 50 may provide support for the adsorptive material coating 46.

The adsorptive material coating 46 of the adsorption layer 50 may define the adsorption flow passage 53, as depicted in FIG. 3. For some embodiments of the present invention, the adsorptive material coating 46 may define at least a portion of the adsorption flow passage 53. The adsorptive material coating 46 may be positioned on and in contact with the adsorption zone fins 58. Additionally, the adsorptive material coating 46 may be positioned on and in contact with the adsorption zone contact portions 59. Further, the adsorptive material coating 46 may be positioned on and in contact with at least a portion of the adsorption zone facing side 62 of the separator plates 52, as depicted in FIG. 3.

Figure 4:
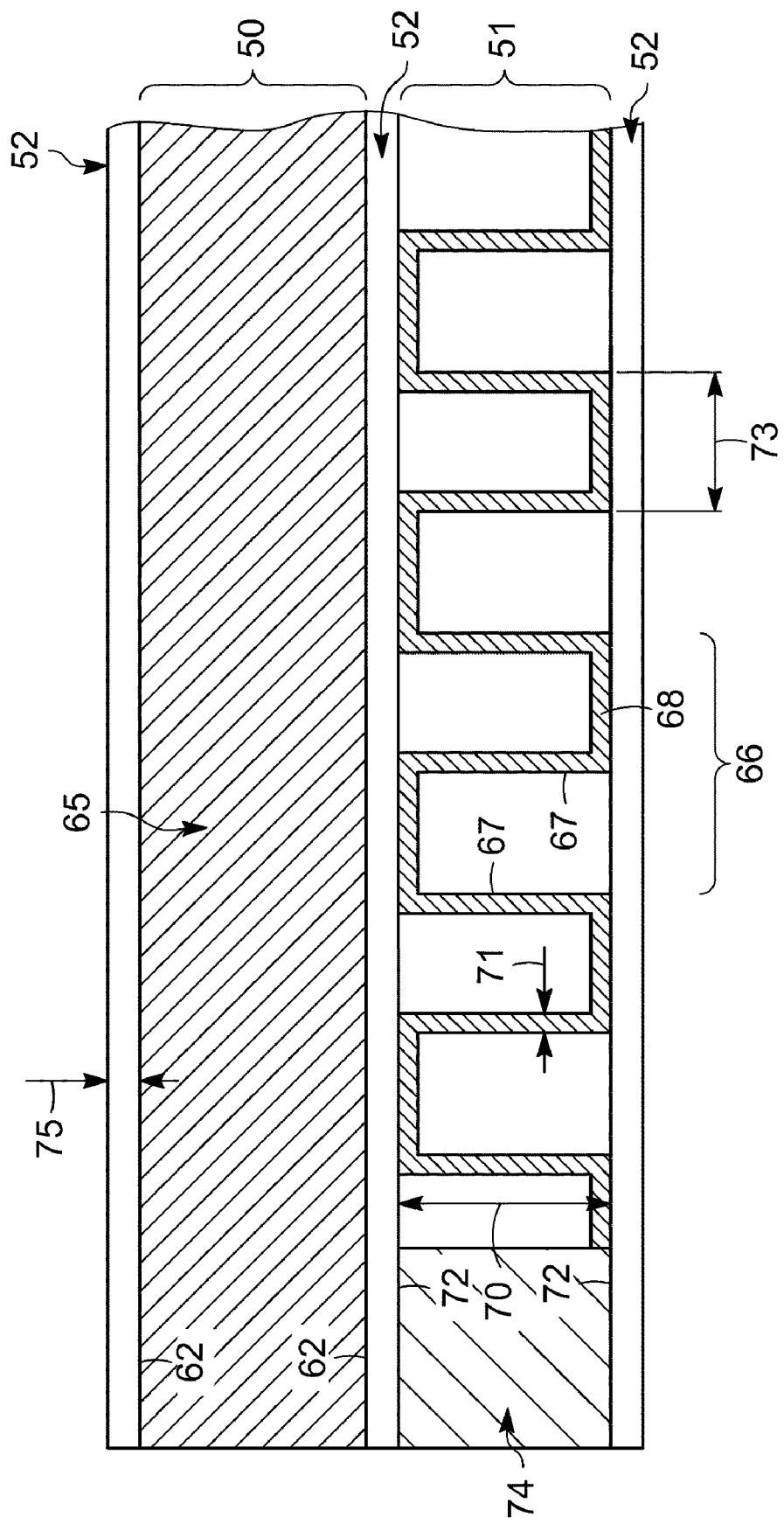
FIG. 4 is a rotated view of FIG. 3.

The heat transfer layer 51 may include a heat transfer zone corrugated sheet 66, as depicted in FIG. 4. The heat transfer zone corrugated sheet 66 may be in contact with and extend between two separator plates 52. The heat transfer zone corrugated sheet 66 may comprise a plurality of heat transfer zone fins 67 and a plurality of heat transfer zone contact portions 68. The heat transfer zone fin 67 may be the portion of the heat transfer zone corrugated sheet 66 that is perpendicular to and extends between the separator plates 52. The heat transfer zone contact portion 68 may be the portion of the heat transfer corrugated sheet 66 that is parallel to and in contact with the separator plate 52.

The heat transfer zone fins 67 may be positioned about perpendicular to the separator plates 52 and may extend about parallel to the heat transfer flow line 56. The heat transfer zone fins 67 may direct the flow of heat transfer fluid 69, as shown in FIG. 2a, through the adsorption heat exchanger 40. The heat transfer zone fins 67 may increase the heat transfer efficiency of the adsorption heat exchanger 40. The heat transfer zone fin 67 may be in contact with and extend between two separator plates 52. The heat transfer fin height 70 may vary with application and may depend on factors including the composition of the heat transfer zone fin 67 and the application. The heat transfer fin thickness 71 may vary with application and may depend on factors including the composition of the heat transfer fluid 69 and the application. The density of heat transfer zone fins (fins/inch) may vary with application and may depend on factors including the composition of the heat transfer fluid 69 and the desired volume of the heat transfer flow passage 55. The density of the heat transfer zone fins 67 may be defined as the number of fins per inch of the heat transfer layer width as measured perpendicular to the heat transfer flow line 56 and parallel to the separator plate 52.

The heat transfer zone contact portions 68 may be positioned about parallel to and in contact with the separator plates 52. The heat transfer zone contact portions 68 may be brazed to a heat transfer zone facing side 72 of the separator plates 52. The heat transfer contact portion width 73 may vary and may depend on the desired density of the heat transfer zone fins 67. The heat transfer contact portion width 73 may be inversely proportion to the density of the heat transfer zone fins 67.

For some applications, in lieu of the heat transfer zone corrugated sheet 66, the heat transfer layer 51 may comprise a plurality of heat transfer zone fins 67 brazed directly to the separator plates 52.

The heat transfer layer 51 may include two heat transfer zone header bars 74, as depicted in FIG. 2a. The heat transfer zone header bars 74 may be positioned parallel to the heat transfer flow line 56. One heat transfer zone header bar 74 may be positioned at one side of the heat transfer layer 51 and the other heat transfer zone header bar 74 may be positioned at the opposing side of the heat transfer layer 51. The heat transfer zone header bars 74 may be brazed to the separator plates 52 and may provide structural support to the adsorption heat exchanger 40.

The heat transfer zone corrugated sheet 66, the heat transfer zone fin 67, the heat transfer zone contact portion 68 and heat transfer zone header bar 74 each may comprise any suitable material, such as but not limited to, aluminized Mylar®, a polymer composite, or a metal. Useful metals may include aluminum, copper, titanium, brass, stainless steel, other light metals and alloys with high conductivity, and graphite fiber composite materials.

Figure 2B:
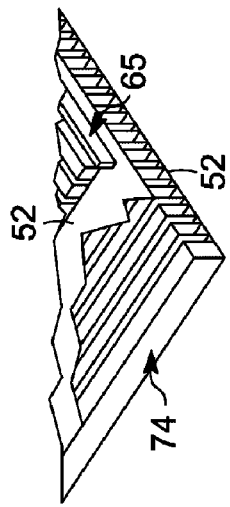
Figure 2C:
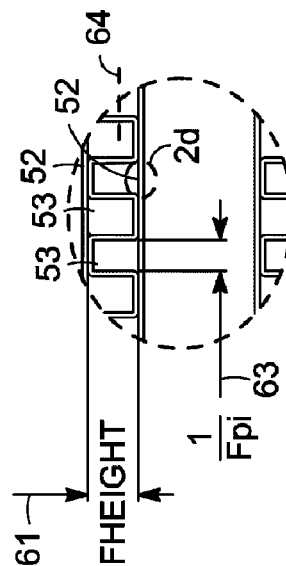
Figure 2D:
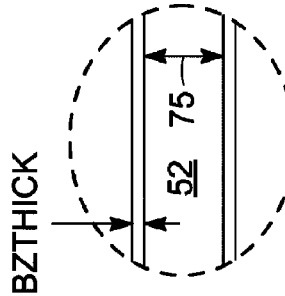
FIG. 2d is a close-up view of a portion of FIG. 2c to show the relationship of a pair of separator plates.

The separator plate 52 of the adsorption heat exchanger 40 may comprise a sheet material structure, as depicted in FIGS. 2a-c. The separator plate 52 may be positioned parallel to the layers 50, 51, as shown in FIGS. 3 and 4. One separator plate 52 may be positioned between and in contact with each adsorption layer/heat transfer layer pair. The separator plate 52 may prevent the flow of adsorbate 60 from entering the heat transfer layer 51 and prevent the flow of heat transfer fluid 69 from entering the adsorption layer 50. The separator plate 52 may comprise any suitable material, such as but not limited to, aluminized Mylar®, a polymer composite, or a metal. Useful metals may include aluminum, copper, titanium, brass, stainless steel, other light metals and alloys with high conductivity, and graphite fiber composite materials.

The width and length of the separator plate 52 may vary and may be about equal to the width and length of the layers 50, 51.

The adsorption heat exchanger 40 further may comprise two side plates 76, as depicted in FIG. 2*a*. The side plates 76 may be positioned parallel to the layers 50, 51. One side plate 76 may be positioned at one side of the adsorption heat exchanger 40 and the other side plate 76 may be positioned at the opposing side of the adsorption heat exchanger 40. The side plates 76 may comprise any suitable material, such as but not limited to, aluminized Mylar®, a polymer composite, or a metal. For some applications, the side plates 76 may be brazed to and provide structural support for the adsorption heat exchanger 40.

Referring back to FIG. 1, a process stream 110 can be directed to either the first temperature controlled adsorber 102 or the second temperature controlled adsorber 104. For illustrative purposes, temperature controlled adsorber 102 will be described as undergoing adsorption, while temperature controlled adsorber 104 will be described as undergoing regeneration. It should be understood that during operation, the temperature controlled adsorbers 102 and 104 are preferably each cycled through alternating adsorption and regeneration steps. Accordingly, when first temperature controlled adsorber 102 is undergoing adsorption, second temperature controlled adsorber 104 is preferably undergoing regeneration. Similarly, when second temperature controlled adsorber 104 is undergoing adsorption, first temperature controlled adsorber 102 is preferably undergoing regeneration. It should also be understood that each temperature controlled adsorber has sufficient connections and feeds to function appropriately when undergoing either adsorption or regeneration, although only a portion of the actual connections to each temperature controlled adsorber are illustrated in FIG. 1.

When first temperature controlled adsorber 102 is undergoing adsorption, process stream 110 is provided to one or more inlets of first temperature controlled adsorber 102. The process stream 110 contains one or more compositional components, at least one of which is desired to be removed through adsorption process. Process stream 110 flows through the one or more adsorption flow passages 106 of the first temperature controlled adsorber 102. The desired compositional component is adsorbed by the adsorptive material coating in the one or more adsorption flow passages 106, and remains as a sorbate on the adsorptive material coating. The sorbate can be adsorbed onto the internal surface of the adsorptive material coating as the process stream 110 flows through the one or more adsorption flow passages 106. The adsorption process thus removes the compositional component from the process stream to produce a product stream 112. Product stream 112 exits the first temperature controlled adsorber 102, and can be utilized in its desired application.

Generally, heat can be produced during the adsorption process, which is commonly known as the heat of adsorption. The heat of adsorption that is generated in first temperature controlled adsorber 102 can be removed by indirect heat exchange with a cooling fluid 114. Cooling fluid 114 is provided to the one or more heat transfer flow passages 108 of the first temperature controlled adsorber 102, removes heat from the one or more adsorption flow passages 106, and exits the first temperature controlled adsorber 102 as heated cooling fluid 116.

When first temperature controlled adsorber 102 is undergoing adsorption, second temperature controlled adsorber 104 undergoes regeneration. During regeneration, second temperature controlled adsorber 104 is isolated from process stream 110. Temperature controlled adsorber 104 undergoes a regeneration cycle after undergoing an adsorption cycle. Once the regeneration cycle is complete, process stream 110 can be once again directed to temperature controlled adsorber 104 to begin another adsorption cycle.

During regeneration, a heating fluid 118 is provided to, and passes through, the one or more heat transfer flow passages 120 of the second temperature controlled adsorber 104. The heating fluid 118 provides heat by indirect heat exchange to the one or more adsorption flow passages 122 of the second temperature controlled adsorber 104. The heat provided by heating fluid 118 is preferably sufficient to provide the regeneration heat requirement for the one or more adsorption flow passages 122. Additionally, the pressure in the one or more adsorption flow passages 122 may be reduced to facilitate regeneration. However, when the pressure is reduced to a sufficiently low value there can be a condition in which there is no need of a regeneration purge gas flow.

To initiate a regeneration cycle, the second temperature controlled adsorber 104 can be isolated from the process stream 110 and the one or more adsorption flow passages 122 can be closed. Heating fluid 118 can be provided to the one or more heat transfer flow passages 120 of the second temperature controlled adsorber 104 to heat the adsorptive coating material to a selected desorption temperature, which is a temperature suitable for desorption of the sorbate. This heating step is preferably substantially isosteric, and can be carried out at an approximately constant sorbed phase concentration or loading level simply by closing valves to disconnect the sorbent passages from both the regeneration stream 126 and regeneration effluent stream 128. Once the adsorptive coating material is at a selected desorption temperature, or after sufficient time has passed to reasonably assume that the adsorptive coating material is at a desired temperature, the one or more adsorption flow passages 122 can be opened to allow regeneration stream 126 to enter. Regeneration stream 126 is preferably gaseous. Regeneration stream 126 can enter and flow through the one or more adsorption flow passages 122. As illustrated, regeneration stream 126 flows through the one or more adsorption flow passages 122 in a direction opposite the direction that the process stream 110 flows through the one or more adsorption flow passages 122 during adsorption. In an alternative embodiment, regeneration stream 126 could flow through the one or more adsorption flow passages 122 in the same direction that the process stream 110 flows through the one or more adsorption flow passages 122 during adsorption. The sorbate that was adsorbed by the adsorptive material coating in the one or more adsorption flow passages 122 during the previous adsorption cycle of the second temperature controlled adsorber 104 is removed from the adsorptive material coating and exits the second temperature controlled adsorber 104 in effluent stream 128. Again one of the features of this invention can be the minimization of the purge gas or regeneration gas flow. Under certain conditions that flow can be brought to zero and the regeneration effluent will have its greatest enrichment in the adsorbed component. The adsorptive material coating can thus be regenerated by removing the sorbate from the temperature controlled adsorber to produce the regeneration effluent stream 128. Regeneration effluent stream 128 can include at least the sorbate and the regeneration stream 126. Regeneration effluent stream 128 can be passed to at least one downstream unit 130 for further processing. Further processing can include, for example, separation of the sorbate from the regeneration stream, if desired.

Heating fluid 118 continues to pass through the one or more heat transfer passages 120 of the second temperature controlled adsorber 104 during the regeneration cycle to provide the heat of desorption. As heating fluid 118 passes through the one or more heat transfer flow passages 120, it loses heat and exits the second temperature controlled adsorber 104 as cooled heating fluid 124.

The flow rate of regeneration stream 126 that is needed can, under the circumstances described above, be referred to as the isothermal stripping gas requirement. The isothermal stripping gas requirement can be directly related to the slope of the isotherm for the sorbate taken at the sorbent temperature and total pressure. Under proper conditions of temperature and pressure the stripping requirement can be driven to zero.

The mole fraction of sorbate in the regeneration effluent stream 128 can be determined by the relationship:

$$Y_{re}=(Y_{ri}+\text{Feed}*(Y_f-Y_p)*t_{ads})/(\#ads*Q'_p*t_{reg})$$

In the equation above, $Y_{ri}$ is the mole fraction of the compositional component in the regeneration inlet, and is generally equal to $Y_p$. The regeneration inlet is the location at which the regeneration stream 126 enters the temperature controlled adsorber 104, and can be, for example, at inlet 132 as shown in FIG. 1. $Y_f$ is the level of the compositional component in the process stream 110, which can be called a feed stream. $Y_p$ is the level of the compositional component in the product stream 112. Feed is the molar feed rate of the process stream 110. $\#_{ads}$ is the number of adsorbers that are in parallel flow during the feed or adsorption step. $Q'_p$ is the flow rate of the purge gas, which is regeneration stream 126, and $t_{reg}$ is the period of time the regeneration stream 126 is flowing through one adsorber. Finally, $Y_{re}$ is the time average effluent mole fraction of the compositional component in the regeneration effluent stream 128.

It is advantageous when $Y_{re}$ is maximized, because it can create efficiencies in the process system, such as, for example, making it easier and less costly to separate the compositional component from the regeneration effluent stream 128. The processes and systems described herein can increase $Y_{re}$ by decreasing $Q'_p$. In a conventional adsorber, such as a packed bed utilized in a TSA or PSA adsorption process, the value of $Q'_p*t_{reg}$ must be large enough to supply all of the heat requirements for regeneration of the adsorber. Those heat requirements include heating the vessel, the bed supports, and the adsorbent material, in addition to supplying the energy to necessary to desorb the sorbate(s). With a temperature controlled adsorber, those heat requirements are supplied by the heating fluid 118 flowing in the one or more heat transfer passages of the temperature controlled adsorber. The value of $Q'_p$ can thus be reduced, because the quantity of regeneration stream 126 is determined not by the heat requirements, but instead by the amount needed to sweep the compositional component, in the form of the sorbate, into the stream and remove it from the adsorber. That value $Q'_p$ can be driven to zero.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

The invention claimed is:

1. A process for sorbate recovery in the adsorption treatment of a process stream, the process comprising:
providing a temperature controlled adsorber that is undergoing a regeneration cycle after undergoing an adsorption cycle, the temperature controlled adsorber having one or more adsorption flow passages and one or more heat transfer flow passages, and the one or more adsorption flow passages containing an adsorptive material coating with a sorbate adsorbed thereto wherein said adsorptive material coating has been applied by a washcoating process;
providing a heating fluid to the one or more heat transfer flow passages of the temperature controlled adsorber; and
regenerating the adsorptive material coating by removing the sorbate from the temperature controlled adsorber to produce a regeneration effluent stream.

2. The process of claim 1 further comprising providing a regeneration stream to the one or more adsorption flow passages of the temperature controlled adsorber.

3. The process of claim 1, wherein the temperature controlled adsorber is a plate-fin type heat exchanger.

4. The process of claim 1, wherein the heating fluid passes through the one or more heat transfer flow passages of the temperature controlled adsorber and exits the temperature controlled adsorber as a cooled heating fluid.

5. The process of claim 1, wherein the heating fluid provides heat by indirect heat exchange to the one or more adsorption flow passages of the temperature controlled adsorber in an amount sufficient to provide the regeneration heat requirement for the one or more adsorption flow passages.

6. The process of claim 2, wherein the regeneration cycle is initiated by isolating the temperature controlled adsorber from a process stream, providing the heating fluid to the one or more heat transfer passages of the temperature controlled adsorber to heat the adsorptive coating material to a desorption temperature, and then passing the regeneration stream to the one or more adsorption flow passages of the temperature controlled adsorber.

7. The process of claim 1, wherein a process stream flows through the one or more adsorption flow passages of the temperature controlled adsorber during an adsorption cycle, and the process stream contains at least one compositional component that is adsorbed by the adsorbent material coating as the sorbate.

8. The process of claim 7, wherein the process stream flows through the one or more adsorption flow passages of the temperature controlled adsorber in a first direction during the adsorption cycle, and the regeneration stream flows through the one or more adsorption flow passages in a second direction opposite the first direction during the regeneration cycle.

9. The process of claim 2, wherein the regeneration stream is gaseous.

10. The process of claim 1, wherein the regeneration effluent stream is passed to at least one downstream unit.

11. The process of claim 1, wherein the sorbate comprises an impurity, a contaminant, a valuable compound, or a regulated compound.

12. The process of claim 1, wherein the sorbate comprises at least one of mercury, one or more volatile organic compounds, water, $CO_2$, $NO_x$, one or more halocarbon refrigerants and propylene.

13. A process for sorbate recovery in the adsorption treatment of a process stream, the process comprising:
providing a temperature controlled adsorber that is undergoing a regeneration cycle after undergoing an adsorption cycle, the temperature controlled adsorber having one or more adsorption flow passages and one or more heat transfer flow passages, and the one or more adsorption flow passages containing an adsorptive material coating with a sorbate adsorbed thereto wherein the adsorptive material coating is applied by a wash coating method;

providing a heating fluid to the one or more heat transfer flow passages of the temperature controlled adsorber, the heating fluid providing heat to the one or more adsorption flow passages of the temperature controlled adsorber by indirect heat exchange;

providing a regeneration stream to the one or more adsorption flow passages of the temperature controlled adsorber; and regenerating the adsorptive material coating by removing the sorbate from the temperature controlled adsorber in a regeneration effluent stream.

14. The process of claim 13, wherein the temperature controlled adsorber is a plate-fin type heat exchanger.

15. The process of claim 13, wherein the regeneration cycle is initiated by isolating the temperature controlled adsorber from a process stream, providing the heating fluid to the one or more heat transfer passages of the temperature controlled adsorber to heat the adsorptive coating material to a desorption temperature, and then passing the regeneration stream to the one or more adsorption flow passages of the temperature controlled adsorber.

16. The process of claim 13, wherein a process stream flows through the one or more adsorption flow passages of the temperature controlled adsorber during an adsorption cycle, and the process stream contains at least one compositional component that is adsorbed by the adsorbent material coating as the sorbate.

17. The process of claim 16, wherein the process stream flows through the one or more adsorption flow passages of the temperature controlled adsorber in a first direction during the adsorption cycle, and the regeneration stream flows through the one or more adsorption flow passages in a second direction opposite the first direction during the regeneration cycle.

18. The process of claim 13, wherein the regeneration stream is gaseous.

19. The process of claim 13, wherein the regeneration effluent stream is passed to at least one downstream unit.

20. The process of claim 13, wherein the sorbate comprises an impurity, a contaminant, a valuable compound, or a regulated compound.

21. The process of claim 13, wherein the sorbate comprises at least one of mercury, one or more volatile organic compounds, water, $CO_2$, $NO_x$, one or more halocarbon refrigerants, and propylene.

\* \* \* \* \*